United States Patent [19]

Johnson

[11] 4,077,845
[45] Mar. 7, 1978

[54] DISPOSABLE INOCULATION DEVICE AND PROCESS OF USING SAME

[75] Inventor: Leighton Clifford Johnson, Edwardsburg, Mich.

[73] Assignee: Miles Laboratories, Inc., Elkhart, Ind.

[21] Appl. No.: 789,203

[22] Filed: Apr. 20, 1977

[51] Int. Cl.² .......................... C12B 1/02; C12K 1/00
[52] U.S. Cl. .................... 195/103.5 K; 195/103.5 M; 195/127
[58] Field of Search ......... 195/103.5 K, 127, 103.5 M

[56] References Cited

U.S. PATENT DOCUMENTS

| 3,957,583 | 5/1976 | Gibson et al. | 195/103.5 K |
| 3,963,355 | 6/1976 | Aldridge et al. | 195/103.5 M |

*Primary Examiner*—Alvin E. Tanenholtz
*Attorney, Agent, or Firm*—Roger N. Coe; Joseph C. Schwalbach

[57] ABSTRACT

A self-contained rehydratable microtiter type device is disclosed in which concentrations of suitable agents are predeposited and dried in growth wells and are then rehydrated with aliquot amounts of the inoculum to be tested. The apparatus and system permit the detection, identification and grouping of urinary tract pathogens.

16 Claims, 9 Drawing Figures

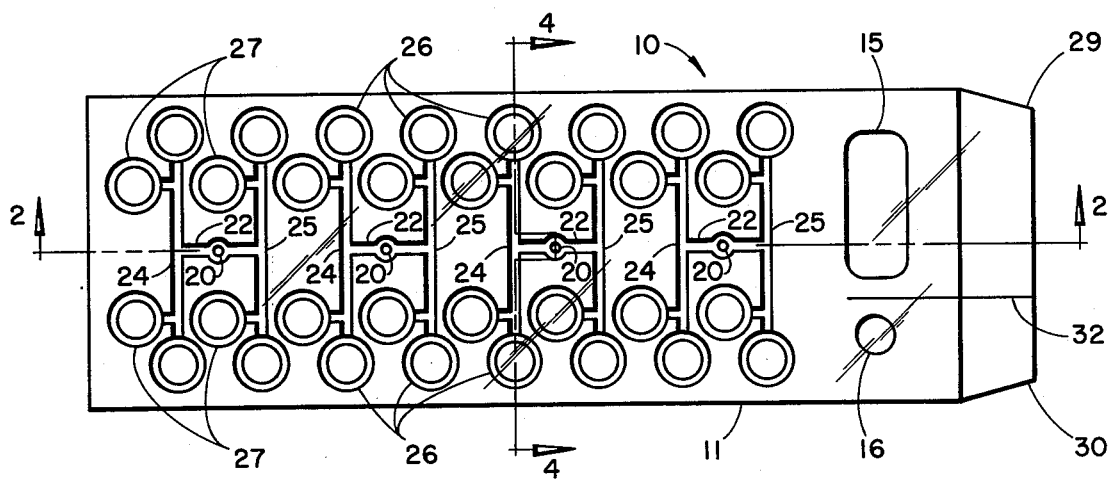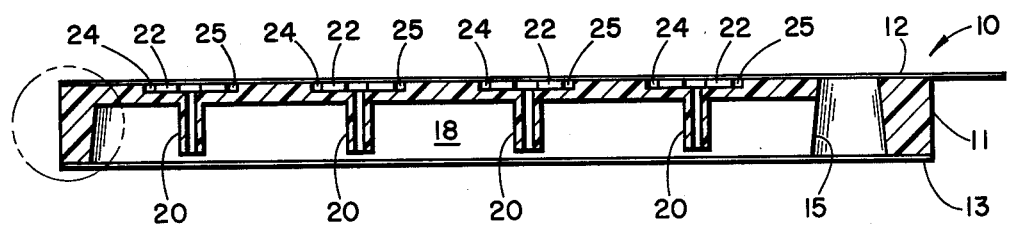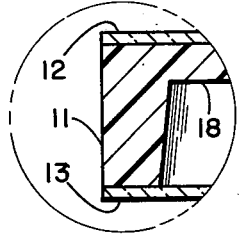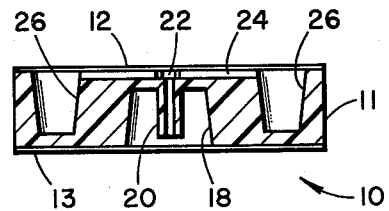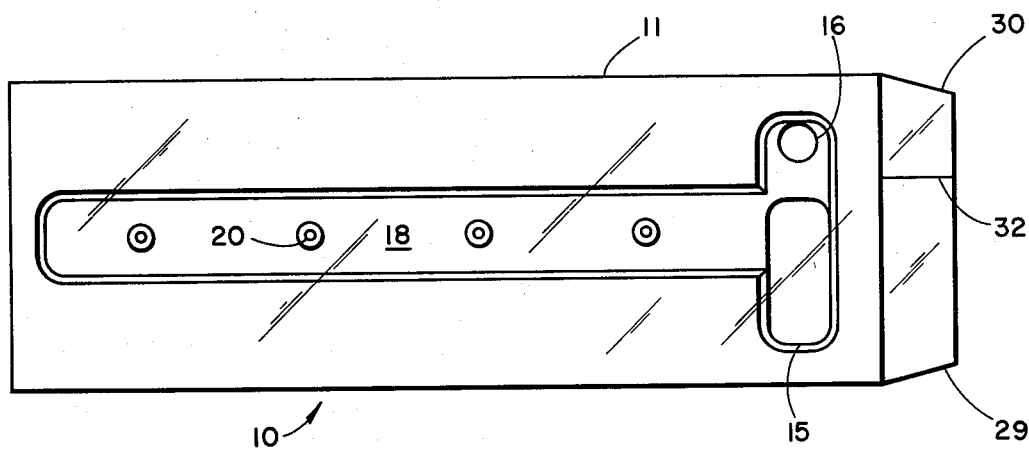
FIG. 1
FIG. 2
FIG. 3
FIG. 4
FIG. 5

DISPOSABLE INOCULATION DEVICE AND PROCESS OF USING SAME

FIELD OF THE INVENTION

The present invention relates to a microtiter type device for use in exposing a test sample to a variety of test reactants and more particularly, the present invention relates to an apparatus and process which are especially adapted for determining the susceptibility of microorganisms to antibiotics.

BACKGROUND OF THE INVENTION

For many years the routine clinical procedure for determining the susceptibility of microorganisms to antibiotics has been a two-step operation requiring a minimum of 48 hours to complete. The first of these steps involves growing the microorganism from a sample and the second step involves subjecting the microorganism to various antibiotics in order to determine which antibiotic inhibits growth of the microorganism. During the time period required to conduct this susceptibility test it is entirely possible that the patient's condition will worsen or change drastically. Accordingly, there has been a recognized need for developing an improved system for determining the susceptibility of microorganisms to antibiotics within a shorter period of time. There has also been a desire for simplifying susceptibility testing and reducing the cost of such tests.

One approach for overcoming these problems is set forth in U.S. Pat. No. 3,957,583 where a cassette for conducting antibiotic susceptibility tests is suggested in which a culture medium is freeze-dried and applied to wells of the cassette. In order to conduct antibiotic susceptibility tests specimens suspected of containing a harmful microorganism are diluted in a predetermined quantity of water in a separate reservoir. The reservoir is then connected with the cassette by means of a needle inserted through a septum. Once the reservoir and cassette are connected a vacuum is drawn through the reservoir, thereby evacuating the interior of the cassette. Upon obtaining the desired vacuum, the upper end of the reservoir is vented to the atmosphere so that pressure on the diluent mixture of microorganism and water contained in the reservoir forces the mixture into the cassette. That diluent mixture flows through various filler passages and completely fills the wells in the cassette where it rehydrates culture medium contained in the wells. In order to fill the wells completely with the diluent mixture overflow cavities are connected to the wells for collecting air remaining in the passageways and wells. While the apparatus and process of the aforementioned patent can be used to significantly shorten the period of time required for making antimicrobial susceptibility determinations there are a number of significant drawbacks which exist with the apparatus and its utilization.

One of the significant drawbacks is the auxiliary equipment required for utilization of the cassettes. For example, a separate, relatively large reservoir interconnected with the cassette through a somewhat complicated needle-septum arrangement is required. In order to avoid any possible cross-contamination this separate reservoir must be replaced for each test. In addition, a relatively expensive vacuum chamber is required for obtaining a proper vacuum inside the cassette. Another disadvantage of the apparatus is the fact that it does not permit varying aliquot amounts of liquid to be used to rehydrate the wells. The cassette is designed in such a manner that the wells are filled up completely each time. Prevention of cross-contamination from well to well is dependent on the existance of inoculum in the feeder lines to the wells and the length of the feeder lines.

SUMMARY OF THE INVENTION

An object of the present invention is to provide an improved apparatus and process for determining the susceptibility of microorganisms to antibiotics.

Another object of the present invention is to provide a self-contained rehydratable microtiter type device which is low in cost and is disposable.

Still another object of the present invention is to provide a simple method for rehydrating multiple growth wells with aliquot quantities of inoculum.

Yet another object of the present invention is to provide a self-contained rehydratable microtiter type device having multiple growth wells which are isolated from each other in such a manner as to prevent cross-contamination.

A still further object of the present invention is to provide a rehydratable device in which antibiotic susceptibility tests can be conducted in less than an 8 hour day.

In accordance with the present invention, a self-contained rehydratable microtiter type device is disclosed in which serial concentrations of material can be predeposited and dried in multiple growth wells or cavities of the device and then a preselected aliquot amount of a chosen inoculum from a reservoir in the device is used to rehydrate the dried material to a proper liquid concentration. Following incubation, if any, the results are observed. For example, by rehydrating dried antimicrobial agents microbial sensitivity can be determined by macroscopically observing turbid growth. Thus, specimen can be introduced into selective culture mediums and known antibiotics. The optical characteristics will change if (a) the specimen contains a microorganism which is favored by the culture medium of the blend and (b) the microorganism is not susceptible to the antibiotic.

BRIEF DESCRIPTION OF THE DRAWINGS

Other and further objects, advantages and features of the invention will be apparent to those skilled in the art from the following detailed description thereof, taken in conjunction with the accompanying drawings in which:

FIG. 1 is a top view of a self-contained rehydratable microtiter type device in accordance with a preferred embodiment of the present invention;

FIG. 2 is a longitudinal vertical cross sectional view taken along line 2—2 in FIG. 1;

FIG. 3 is an enlarged cross sectional view of a portion of FIG. 2 indicated in phantom outline;

FIG. 4 is a transverse vertical cross section view taken along the line 4—4 in FIG. 1;

FIG. 5 is a bottom view of the self-contained rehydratable microtiter type device illustrated in FIG. 1;

DESCRIPTION OF THE PREFERRED EMBODIMENTS

Figure 6:
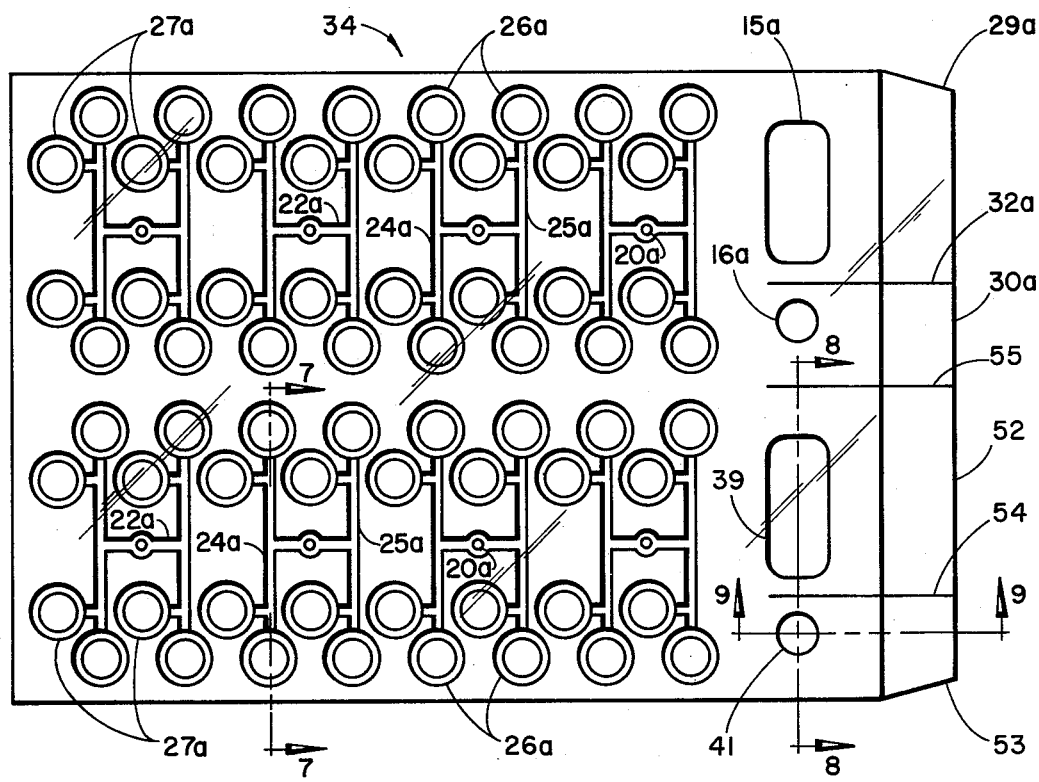
FIG. 6 is a top view of another embodiment of the present invention which is similar to the device illustrated in FIG. 1.
Figure 7:
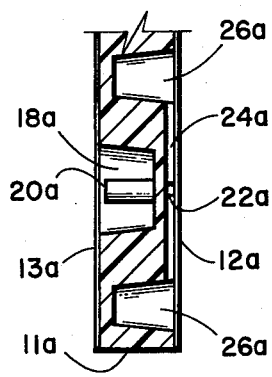
FIG. 7 is a cross sectional view, partially broken away, taken along line 7—7 of FIG. 6.
Figure 8:
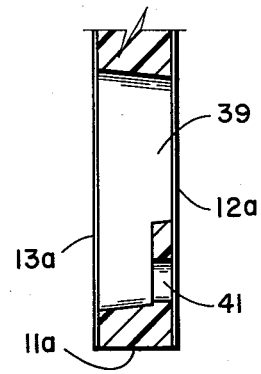
FIG. 8 is a cross sectional view, partially broken away, taken along line 8—8 of FIG. 6.

Referring now to the drawings, a self-contained rehydratable microtiter type device in accordance with the present invention is illustrated by disposable inoculation device 10 of FIGS. 1-5. Disposable inoculation device 10 is shown as a plate having upper and lower surfaces; a central manifold chamber disposed along the lower plate surface; a filling port located in the upper plate surface, the port being interconnected with said central manifold chamber; separate growth wells located in the upper plate surface; siphon tubes extending from near the upper plate surface into the central manifold chamber; a plurality of grooves in the upper plate surface which interconnect the growth wells and siphon tubes; an aspiration bore located in the upper plate surface, the bore being interconnected with the central manifold chamber; and separate transparent covering means sealing the upper and lower plate surfaces.

The disposable inoculation devices of this invention are designed especially for conducting antibiotic susceptibility tests, i.e., tests to determine the effect of known antibiotics on microorganisms which are subsequently introduced into the inoculation device. Based on color characteristics, tubidity and precipitation reactions it is possible to analyze very selectively for the following organisms which account for the vast majority of pathogens found in urinary tract infections: *Pseudomonas aeruginosa, Proteus spp., Citrobactor freundii, Serratia spp., Escherichia coli, Klebsiella/Enterobacter,* Yeasts, Enterococcus Group D, *Staphylococcus aureaus.* Antibiotics which can be tested with these organisms include ampicillin, cephalothin, chloramphenicol, gentamycin, kanamycin, polymixin and tetracycline.

Referring more specifically to the drawings, inoculation device 10 illustrated in FIGS. 1 to 5 is shown as comprising an elongated generally rectangular shaped block or plate 11 measuring, for example, about 147mm long by about 52mm wide and about 13mm thick. As will be described hereinafter tape members 12 and 13 cover the upper and lower surfaces, respectively, of plate 11.

plate 11 is formed in its upper surface with a plurality of frustoconically shaped growth wells 26 and 27 and is formed in its lower surface with a T-shaped manifold or reservoir channel 18. The T-shaped channel 18 has an elongated stem portion disposed along the longitudinal center line of plate 11 for substantially the entire length thereof, and a transverse portion disposed adjacent one end of plate 11 as best shown in FIGS. 2 and 5. The longitudinally extending portion of channel 18 is about 12.2 centimeters in length, and the transversely extending portion of said channel is about 4 centimeters in length, each of said channel portions having a width of about 1.4 centimeters and depth of about 1.0 centimeter.

As best shown in FIGS. 2 and 4, a plurality of regularly spaced siphon tubes 20 are arranged along the longitudinal center line of plate 11 and depend from the upper surface of channel 18, tubes 20 terminating at their lower ends adjacent, but spaced from, the plane of the lower surface of plate 11. The illustrated siphon tubes have an inside diameter of approximately 1.0 millimeter.

The upper surface of plate 11 is formed with spaced transverse grooves 24 and 25 having branched opposite ends each communicating with wells 26 and 27. The upper surface of plate 11 is also formed with a plurality of longitudinally extending grooves 22 each of which connects groove 24 and 25 with the bore of siphon tube 20, as shown. An appropriate size for the grooves 22, 24 and 25 has been found to be about 1.25 centimeters in width and about 0.65 centimeter in depth.

A rectangular shaped filling port or opening 15, measuring about 2.5 centimeters by about 1.0 centimeter, is formed in the upper surface of plate 11 and opens into the transversely extending portion of T-shaped channel 18. Opening 15 is large enough to permit a specimen (i.e., inoculum) to be poured into channel 18 from a container such as a test tube, after covering tape member 12 is removed from opening 15, as hereinafter described. Plate 11 is also formed in its upper surface with a smaller circular opening 16, measuring about 0.5 centimeter in dimeter, which is preferably located over and opens into the transversely extending portion of the T-shaped channel 18. Opening 16 is an aspiration bore designed for interconnection with a syringe (not shown) upon removal of tape member 12 from said openings in a manner described hereinafter.

In practice, inoculum or specimen introduced through opening 15, after removal of tape member 12, fills at least a portion of the reservoir formed by channel 18 and covering tape 13. Sufficient inoculum is introduced to cover the lower ends of the four siphon tubes 20 which, with grooves 22, 24 and 25, provide flow passage means for transmission of inoculum from reservoir 18 to detection or growth wells 26 and 27.

In the illustrated embodiment one siphon tube 20 and one set of passages 22, 24 and 25 are shown for each eight growth wells. Tape member 12 seals the upper surface of plate member 11 as aforementioned, and converts the interconnecting channels in the upper surface of plate 11 into the geometric equivalent of an array of spaced capillary tubes.

Tape member 12 also covers growth wells 26 and 27. These wells are formed along the outer perimeter of inoculation device 10 so as to have substantially equidistant flow passage connection with siphon tubes 20, the top of the wells being coplanar with the upper surface of member 11. These growth wells can be formed by drilling or boring the wells perpendicular to the plane of the upper surface of member 11 such that wells 26 and 27 extend approximately three quarters of the way through member 11. The size of the growth wells is not critical, especially since the desired objective is to place an aliquot amount of liquid into the growth wells rather than completely fill the wells. It will be understood, however, that if desired the wells could be substantially filled.

Tape members 12 and 13 can be compatible transparent pressure sensitive tape. Acetate, polyester, polyolefin, saran, nylon or other tape materials are suitable for this purpose. A particularly suitable tape is Mylar, manufactured by E. I. duPont de Nemours Company, Inc. Another suitable tape is No. 355-2, which is manufactured by the 3M Company.

A portion of tape member 12 extends outwardly from the end of plate 11 adjacent to openings 15 and 16 forming tabs 29 and 30 separated by slit 32. The combination of tabs 29 and 30 together with slit 32 permits pressure sensitive tape 12 to be pulled back from the upper surface of plate 11 exposing opening 15 or opening 16, as required, during the utilization of the inoculation device. The pressure sensitive tape can then be reapplied to the upper surface of plate 11, thereby resealing opening 15 or 16. If desired, tabs members 29 and 30 can be reinforced with suitable material, such as paper, to stiffen the tab members and thereby facilitate their utilization.

In operation, inoculum is drawn up from reservoir 18 through siphon tubes 20 into growth wells 26 and 27, using means for creating a vacuum in a manner described hereinafter. It will be understood that the number of growth wells and the arrangement shown, wherein a plurality of groups or rows extend axially in two columns along two outer sides of plate 11, is a matter of choice. If desired, a siphon tube could be present for each growth well, each pair of growth wells, or any plurality thereof. The use of one siphon tube for eight growth wells has been found to work very satisfactorily.

While it has been found particularly advantageous to arrange the growth wells linearly in parallel rows as in FIG. 1 it will be understood that circular trays, U-shaped trays and other arrangements (not shown) can be used. For example, in a circular or U-shaped arrangement inoculum is introduced into a central reservoir of such an arrangement which can be connected by channels to growth wells located along the curved perimeter of the tray.

While plate 11 is shown as a solid block of plastic which has been suitably machined to provide the desired configuration of filling passages, reservoirs, openings, growth wells and the like, it will be understood that plate 11 could readily be molded or otherwise fabricated to obtain the desired configuration. Molding would permit elimination of unnecessary material present in illustrated plate 11 and would thereby decrease the weight and cost of inoculation device 10. While any suitable material can be used for plate 11, the material must be substantially transparent in the area of the growth wells in order that one can observe color changes, tubidity and precipitation reactions occurring in said growth wells. Polystyrene is a plastic material especially suitable for use in making plate 11. Other suitable materials include polymethylmethacrylate, polycarbonate and polyacetate.

Disposable inoculation device 34 illustrated in FIGS. 6-9 is another form of an inoculation device similar to inoculation device 10 illustrated by FIGS. 1-5. Parts corresponding to those of FIGS. 1-5 are indicated in FIGS. 6-9 by the same numerals bearing the suffix a. For example, inoculation device 34 has elongated tray member or plate 11a with self adhesive tape members 12a and 13a covering, respectively, its upper and lower surfaces. The upper surface of plate 11a has openings 15a and 39 for the introduction of inoculum and openings 16a and 41 for interconnection with a vacuum device, such as syringe 57 illustrated in FIG. 8. Siphon tubes 20a extend from reservoir area 18a of 11a to feeder tubes 22a which are interconnected to growth wells 26a and 27a via feeder passageways 24a and 25a. In FIG. 6 four separate and distinct end tabs 29a, 30a, 52 and 53 are illustrated. These tabs are separated by slits 32a, 55 and 54, respectively. The function of elements in the embodiment illustrated in FIGS. 6-9 is identical to that of corresponding elements in FIGS. 1-5. The main difference between the embodiments is the number of growth wells present. Plate 11a of FIGS. 6-9 is the equivalent of two plates 11 of FIG. 1 secured together in side-by-side relation.

Figure 9:
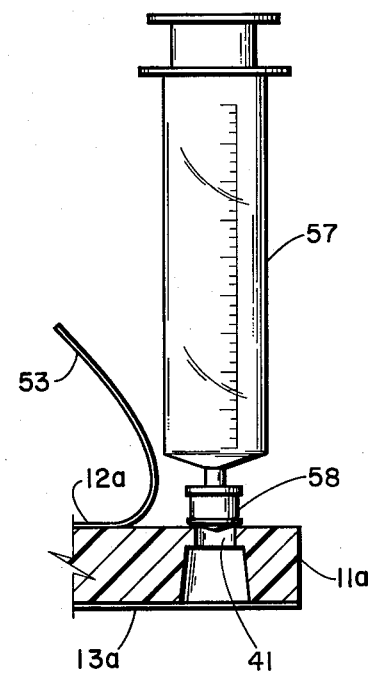
FIG. 9 is a cross sectional view, partially broken away, taken along line 9—9 in FIG. 6 and includes a syringe positioned over a syringe port for creating a vacuum in the device.

In FIG. 9 tab 53 is pulled back, thereby lifting the adjacent portion of pressure sensitive tape member 12a and uncovering opening 41 in the upper surface of plate 11a. This permits syringe 57 or a like device to be placed down over opening 41 in such a manner that rubber seal adapter 58 effectively seals the opening. The syringe can then be used to draw a vacuum in the inoculation device. Upon release of that vacuum an aliquot amount of inoculum previously introduced into reservoir 18a through opening 39 is distributed into connected growth wells 26a and 27a. Following the distribution of aliquot portions of inoculum into the growth wells, syringe 57 can be removed from syringe port or opening 41 and pressure sensitive member 12a is reapplied to the upper surface of plate 11a in order to once again seal opening 41.

It will be understood that the procedure specified with respect to openings 39 and 41 can be applied to openings 15a and 16a such that tests can be made simultaneously in both sides of device 34.

Thus, to use the inoculation device described herein after the devices have been loaded with the desired antimicrobial material, the user must first peel back tape covering an inoculum opening and pour into that opening a fixed amount, e.g., 8 milliliters, of inoculum. The covering tape is then pressed back into place over the inoculum reservoir and the tape covering the associated syringe port or opening is peeled back to uncover that opening. A vacuum can be obtained using suitable means, such as a 12 milliliter syringe with a rubber seal adapter placed on the Leur end and pressed over the syringe opening. The syringe piston is withdrawn a desired amount, e.g., to the 11 milliliter mark. This withdrawal of the piston evacuates air from the growth wells and flow passages through the siphon tubes, and upon return of the syringe piston to its fully depressed original position, air entering the inoculum reservoir creates a pressure which forces an aliquot portion of inoculum from said reservoir through the siphon tubes and flow passages to each of the growth wells. For example, using the inoculation device of FIGS. 1-5 about 100 microliters of inoculum can be placed in each growth well following the described procedure. The syringe port or opening is then recovered and sealed with the covering tape.

Thus, culture medium freeze-dried in the growth wells is rehydrated by introduction thereinto of liquid specimen or inoculum. Following incubation growth, color change and/or precipitation are observed. Certain culture mediums undergo an optical change as a result of the metabolic action of specific microorganisms. While the favored microorganism will grow or multiply in the selective medium, growth is not necessary to effect an optical change. Only a specific microorganism will live and propagate in the culture medium and will cause optical change. Hence, when optical change is observed it is apparent that the specific microorganism is living in the culture medium.

Whereas the 32 growth well model inoculation device illustrated in FIGS. 1-5 is a configuration which permits susceptibility testing, for example, with four antimicrobials of seven dilutions with a control well for each antimicrobial, the 64 growth well configuration of FIGS. 6-9 could contain serial dilutions of eight antimicrobials of 14 dilutions with a control well for each antimicrobial. By loading the inoculation devices with appropriate antimicrobial solutions and then dehydrating those solutions, the devices, which are completely sealed with transparent self-adhesive tape, can be sterilized and sold as unitized test systems.

Since the culture medium is freeze-dried, the tray or inoculation device can be stored for relatively long periods of time. The culture medium must be rehydrated before it is capable of promoting growth of the specific microorganism and changing its light transmitting characteristics. It is desirable to have at least one of the growth wells contain only culture medium by itself. Culture medium in the remaining wells can have antibiotic blended with it. The antibiotics can vary from well to well and two different wells can have the same antibiotics, but at different strengths. The microorganisms will not live or propagate in those wells containing an antibiotic to which the favored microorganism is susceptible, provided the antibiotic is present in sufficient strength.

Changes in the optical characteristics of the growth wells can be observed with the naked eye or with optical detection equipment. One form of such optical detection equipment projects light through the wells and measures the intensity of light passing through the wells. A signficant decrease in intensity indicates growth or metabolic action of the favored microorganism in the growth well and hence the fact that the antibiotic in the growth well is not effective against the favored microorganism.

From the foregoing, it will be seen that this invention is adapted to attain all of the ends and objects hereinabove set forth, together with other advantages which are obvious and inherent. In accordance with the invention, pathogens can be detected, identified, grouped and enumerated rapidly using specimens directly for inoculation of selective media. The selective media can be freeze-dried and especially formulated for specific organisms commonly encountered in clinical urine specimens. In addition, positive controls are possible and all of the growth wells are reconstituted simultaneously in aliquot amounts. Growth in individual growth wells permits a positive test for indication of organisms.

The apparatus and system can be utilized for analyzing sputeum, throat and fecal specimens, blood and spinal fluid, as well as for urine analysis. The apparatus of the present invention can also be used in other clinical areas such as blood typing, immunological testing, clinical chemistry, serology, virology, and the like, whenever it is necessary to expose a test sample to a variety of test reactants.

The rehydratable device of this invention is sufficiently low in cost to be disposable. The device is also self-contained, it can be sterilized, it is transparent, it can be hermetically sealed for product stability, it is completely resealable after inoculation in order to prevent contamination and assure user safety, it is adaptable to low-cost manufacturing methods, it permits the simple and safe disposal of completed tests and it permits the isolation of growth wells to prevent cross-contamination.

While the preferred form of the invention uses pressure sensitive tape to seal the upper and lower surface of a plate it will be understood other means (including transparent solid members) could, if desired, be used to cover these surfaces. The plate could even be formed into two sections, i.e., an upper section and a lower section, joined together and sealed in a suitable manner.

Whereas aerobic types of microorganisms require oxygen, anaerobic types are able to live and reproduce in the absence of air or oxygen. The present invention can be adapted to be used with anaerobic microorganisms by providing a septum across the aspiration bore and employing a syringe with a needle to pierce the septum. Moreover, self-sealing tape used to seal the upper surface of inoculation apparatus in accordance with the present invention could be perforated by the needle on the end of a syringe without ever removing the tape from the aspiration bore.

Obviously, many modifications and variations of the invention as hereinabove set forth can be made without departing from the spirit and scope thereof and therefore only such limitations should be imposed as are indicated by the appended claims.

What is claimed is:

1. Inoculation apparatus comprising a plate formed with at least one sealed growth well, said plate being formed with a sealed reservoir, at least one siphon tube projecting into said reservoir and terminating adjacent the bottom thereof, flow passage means communicating between said siphon tube and an upper portion of said growth well, said plate being provided with aperture means communicating with said reservoir and having a first portion through which liquid inoculum can be introduced into said reservoir, said aperture means also having a second portion adapted for connection with pump means, and removable closure means for sealingly closing each of said first and second portions of said aperture means following connection of said second aperture means portion with pump means and after introduction into said reservoir of an amount of liquid inoculum sufficient to provide a liquid level in said reservoir above the lower end of said siphon tube, withdrawal by said pump means of a predetermined volume of air from said reservoir causing evacuation of air from said growth well, flow passage means and siphon tube, and the subsequent introduction of a predetermined quantity of air into said reservoir by said pump means causing liquid inoculum to be forced from said reservoir through said siphon tube and passage means to said growth well.

2. The inoculation apparatus of claim 1 in which the first portion of said aperture means comprises a filling port formed in the upper surface of said plate.

3. The inoculation apparatus of claim 1 in which the second portion of said aperture means comprises an aspiration port formed in the upper surface of said plate.

4. The inoculation apparatus of claim 1 in which the passage means comprise grooves formed in the upper surface of said plate which are covered by a layer of pressure sensitive tape means sealed to the upper surface of said plate.

5. The inoculation apparatus of claim 1 in which a plurality of growth wells are present connected by equidistant flow passage means to said siphon tube.

6. The inoculation apparatus of claim 1 in which at least a wall portion of said growth well is transparent.

7. The inoculation apparatus of claim 1 having a plurality of growth wells comprising recesses formed in the upper surface of said plate, said recesses being covered by transparent layer of pressure sensitive tape means sealed to the upper surface of said plate.

8. The inoculation apparatus of claim 1 in which said reservoir comprises a recess formed in the bottom surface of said plate, said recess being covered by a layer of pressure sensitive tape sealed to the bottom surface of said plate.

9. Inoculation apparatus comprising:
a plate having upper and lower surfaces;
a central manifold chamber disposed along the lower surface of said plate;
a filling port located in the upper surface of said plate, said filling port being interconnected with said central manifold chamber;
siphon tubes extending from near the upper surface of said plate into said central manifold chamber;
separate growth wells located in the upper surface of said plate;
a plurality of grooves in the upper surface of said plate, each of said grooves having an outlet end connected with a growth well and an inlet end interconnected with a siphon tube;
an aspiration bore located in said upper surface, said aspiration bore being connected with said central manifold chamber and adapted to being connected to means for applying a vacuum to said growth wells;
first covering means having a first and second tab at one end, said first covering means sealingly engaging said upper surface of said plate thereby forming with said grooves a plurality of sealed tube-like channels connecting the siphon tubes with the growth wells and forming a cover for said growth wells, filling port and aspiration bore, said first covering means being split at one end so as to enable the first covering means to be pulled back by means of said first tab from said filling port or by means of said second tab from the aspiration bore and then being resealed;
a second covering means sealingly engaging said lower surface of the plate thereby forming a cover on said central manifold chamber.

10. The apparatus of claim 9 wherein said first and second transparent covering means comprise separate sheets of clear plastic adhesively mounted to the upper and lower surfaces, respectively.

11. The apparatus according to claim 10 wherein said sheets of clear plastic are made from transparent pressure sensitive tape.

12. Apparatus for conducting antibiotic susceptibility tests on clinical specimens, said apparatus comprising:
an elongated plate having substantially parallel upper and lower surfaces,
a central manifold chamber disposed along a portion of the lower surface of said plate;
a filling port located in the upper surface of said plate, which port is connected with said central manifold chamber;
an aspiration bore located adjacent to said filling port in the upper surface of said plate, said aspiration bore being connected with said central manifold chamber;
siphon tubes extending perpendicularly from near the upper surface of said plate into said central manifold chamber;
individual detection wells disposed along the upper surface of said plate;
filler passageways leading from said siphon tubes to said detection wells;
means for isolating said detection wells, said filler passageways, said filling port and said aspiration bore from the surrounding atmosphere on the upper surface of said plate;
means for isolating the central manifold chamber from the surrounding atmosphere on the lower surface of said plate; and
a blend of culture medium and known antibiotics in at least some of the detection wells, the culture medium being sensitive to a microorganism such that the optical characteristics of the culture medium changes when the microorganism is sustained in the culture medium, said culture medium further being selective in that it undergoes a change in optical characteristics only when a specific microorganism is sustained by it.

13. Apparatus for conducting antibiotic susceptibility tests on clinical specimens, which apparatus comprises:
a plate having a plurality of detection wells opening out of an upper surface thereof with the wells being visible on both sides of the plate so light can pass through the apparatus at the location of the wells, said plate also having a filling port, an aspiration bore and a central manifold chamber, said filling port and aspiration bore being interconnected with said central manifold chamber such that clinical specimens can be poured into the central manifold chamber through the filling port and air can be evacuated from the detection wells through the aspiration bore;
siphoning means extending from the upper surface in said plate down into said central manifold chamber and filler passageways leading from said siphoning means to the detection wells, said siphoning means and said filler passageways adapted to transmit clinical specimens from said central manifold chamber to said detection wells;
a selective culture medium in said detection wells with known antibiotics blended with the culture medium in at least some of the wells, the culture medium being selective in the sense that the light transmitting characteristics of the culture medium will change when the clinical specimen contains a microorganism to which the culture medium is specific, and
transparent closing means applied to surfaces of said plate for isolating the plate from the surrounding atmosphere.

14. A process for determining the susceptibility of specific microorganisms to antibiotics, said process comprising:
removing a first tape member from one end of a microtiter tray formed with a sealed manifold chamber, separate growth wells, at least one siphon tube projecting into said manifold chamber and terminating adjacent the bottom thereof, flow passage means communicating between said siphon tube and upper portion of said growth wells, and aperture means communicating with said manifold chamber, said aperture means having a first filling portion covered by said first tape member and a second portion covered by a second tape member, said second portion adapted for connection with pump means; introducing a clinical specimen containing microorganisms into said central manifold chamber of said tray;
resealing the first tape member and removing a second tape member from said microtiter tray;
evacuating air from said growth wells in which a selective culture medium is contained and from wells in which blends of the selective culture medium and known antibiotics are contained, said culture medium favoring the specific microorganism such that the light transmitting characteristics of a mixture of the culture medium and water will change when the favored microorganism is sustained within and nourished by the medium;

replacing the evacuated air with an aliquot mixture of said clinical specimen from said central manifold chamber and resealing said second tape member;

incubating the tray; and observing the growth wells for change in the light transmitting characteristics thereof.

15. The process according to claim 14 wherein the culture medium is freeze-dried and water present in the clinical specimen rehydrates the culture medium.

16. The process according to claim 14 wherein change in the light transmitting characteristics of the growth wells is observed by projecting light through said wells and measuring the intensity of the light passing through said growth wells.

* * * * *